United States Patent [19]
Weitz et al.

[11] Patent Number: 6,075,013
[45] Date of Patent: Jun. 13, 2000

[54] MODIFIED LOW MOLECULAR WEIGHT HEPARIN THAT INHIBITS CLOT ASSOCIATED COAGULATION FACTORS

[75] Inventors: Jeffrey I. Weitz, Ancaster; Jack Hirsh, Hamilton, both of Canada

[73] Assignee: Hamilton Civic Hospitals Research Development Inc., Hamilton, Canada

[21] Appl. No.: 09/092,325

[22] Filed: Jun. 5, 1998

Related U.S. Application Data

[60] Provisional application No. 60/072,098, Jun. 6, 1998, abandoned.

[51] Int. Cl.$^7$ .................................................. A61K 31/725
[52] U.S. Cl. .............................. 514/56; 514/54; 514/921; 536/21; 536/122; 536/123.1; 536/124
[58] Field of Search .............................. 435/69.6; 514/56, 514/54, 921; 536/21, 122, 123.1, 124

[56] References Cited

U.S. PATENT DOCUMENTS

| | | | |
|---|---|---|---|
| 4,303,651 | 12/1981 | Lindahl et al. | 424/183 |
| 4,486,420 | 12/1984 | Lormeau et al. | 424/183 |
| 4,629,699 | 12/1986 | Bianchini | 435/101 |
| 4,687,765 | 8/1987 | Vairel et al. | 514/56 |
| 4,981,955 | 1/1991 | Lopez | 514/56 |
| 4,990,502 | 2/1991 | Lormeau et al. | 514/56 |
| 5,084,564 | 1/1992 | Vila et al. | 514/56 |
| 5,707,973 | 1/1998 | Baron et al. | 514/56 |
| 5,721,357 | 2/1998 | Baron et al. | 536/124 |
| 5,744,457 | 4/1998 | Weitz et al. | 514/54 |
| 5,763,427 | 6/1998 | Weitz et al. | 514/54 |
| 5,767,269 | 6/1998 | Hirsh et al. | 514/56 |
| 5,849,721 | 12/1998 | Uzan | 514/56 |

FOREIGN PATENT DOCUMENTS

| | | |
|---|---|---|
| 0 244 235 | 11/1987 | European Pat. Off. . |
| 0 287 477 | 10/1988 | European Pat. Off. . |
| 0 337 327 | 10/1989 | European Pat. Off. . |
| 0 511 075 | 10/1992 | European Pat. Off. . |
| 0 735 050 | 10/1996 | European Pat. Off. . |
| 29 44 792 | 5/1990 | Germany . |
| WO 93/16112 | 8/1993 | WIPO . |

*Primary Examiner*—F. T. Moezie
*Attorney, Agent, or Firm*—Townsend and Townsend and Crew LLP

[57] ABSTRACT

The present invention provides compositions and methods for the treatment of cardiovascular diseases. More particularly, the present invention relates to modifying thrombus formation by administering an agent which, inter alia, is capable of (1) inactivating fluid-phase thrombin and thrombin which is bound either to fibrin in a clot or to some other surface by catalyzing antithrombin; and (2) inhibiting thrombin generation by catalyzing factor Xa inactivation by antithrombin III (ATIII). The compositions and methods of the present invention are particularly usefull for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, etc.

39 Claims, 13 Drawing Sheets

MODIFIED LOW MOLECULAR WEIGHT HEPARIN THAT INHIBITS CLOT ASSOCIATED COAGULATION FACTORS

This patent application is a continuation-in-part of U.S. Provisional Patent Application Ser. No. 60/072,098 filed Jun. 6, 1998, now abandoned, the teachings of which are incorporated herein by reference

FIELD OF THE INVENTION

The present invention relates generally to compositions and methods for the treatment of cardiovascular disease. More particularly, the present invention relates to modifying thrombus formation and growth by administering a modified low molecular weight heparin (MLMWH) that, inter alia, is capable of (1) inactivating fluid-phase thrombin as well as thrombin which is bound either to fibrin in a clot or to some other surface by catalyzing antithrombin; and (2) inhibiting thrombin generation by catalyzing factor Xa inactivation by antithrombin III (ATIII). In addition, the present invention provides methods and compositions useful for treating cardiovascular disease.

BACKGROUND OF THE INVENTION

Blood coagulation is a process consisting of a complex interaction of various blood components, i.e., factors, that eventually gives rise to a fibrin clot. Generally, the blood components which participate in what has been referred to as the coagulation "cascade" are proenzymes or zymogens, i.e., enzymatically inactive proteins that are converted to proteolytic enzymes by the action of an activator which is, itself, an activated clotting factor. Coagulation factors that have undergone such a conversion are generally referred to as "activated factors," and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, i.e., pathways, that promote the activation of Factor X. The "intrinsic pathway" refers to those reactions that lead to thrombin formation through utilization of factors present only in plasma. A series of protease-mediated reactions ultimately generates Factor IXa that, in conjunction with Factor VIIIa, cleaves Factor X into Xa.

An identical proteolysis is effected by Factor VIIa and its co-factor, tissue factor, in the "extrinsic pathway" of blood coagulation. Tissue factor is a membrane bound protein and does not normally circulate in plasma. Upon vessel disruption, however, it can complex with Factor VII or Factor VIIa to catalyze Factor X activation or Factor IX activation in the presence of $Ca^{2+}$ and phospholipid. While the relative importance of the two coagulation pathways in hemostasis is unclear, Factor IX activation by the Factor VIIa-tissue factor complex has, in recent years, been found to play a pivotal role in the propagation of the normal clotting response. As such, Factor IX activation in response to tissue factor exposed at sites of vascular injury can contribute to thrombosis, a pathological manifestation of the clotting cascade in blood vessels.

Thrombosis, which can complicate rupture of an atherosclerotic plaque, can cause partial or total occlusion of the affected blood vessel, thereby leading to a number of important cardiovascular complications, including unstable angina, acute myocardial infarction (heart attack), or cerebral vascular accidents (stroke). Vessel injury and/or stasis can trigger venous thrombosis causing deep vein thrombosis and subsequent pulmonary embolism. Such diseases are a major cause of disability and mortality throughout the world, but particularly in Western societies. Moreover, thrombin and, in particular, surface-bound thrombin play a role in thrombus formation in cardiac bypass circuits, after angioplasty and during and after thrombolytic therapy for acute myocardial infarction. Therefore, patients undergoing these procedures must be treated with very high doses of anticoagulants or other antithrombotic agents. Although high doses of these agents may effectively prevent clotting, they can give rise to serious bleeding complications.

The clot or thrombus, which forms as a result of activation of the clotting cascade, contains fibrin, platelets and numerous other blood components. Thrombin bound to fibrin remains active and causes growth of the clot by continued cleavage of fibrinogen and activation of platelets and other coagulation factors, such as factor V and factor VIII. Moreover, unlike free thrombin which is readily inactivated by naturally occurring anti-thrombins (e.g., antithrombin III (ATIII)), clot-bound thrombin is protected from inactivation. As a result, the clot acts as a reservoir for active thrombin that triggers further clot growth. In addition, thrombin also induces smooth cell proliferation and, thus, may be involved in proliferative responses, such as graft-induced atherosclerosis and restenosis after angioplasty or atherectomy.

Because thrombin is critical to thrombus formation, the use of thrombin inhibitors for treating thrombosis and thrombotic complications has long been proposed. A number of partially effective inhibitors have been in use for years. Heparin, for example, can be used as an anticoagulant and antithrombin agent to inhibit fibrin formation, platelet aggregation and thrombus formation. Heparin, however, has a number of limitations. For example, it has biophysical limitations because it acts as an anticoagulant by activating ATIII and, thus, it is relatively ineffective at inactivating fibrin-bound thrombin when given in safe doses. Consequently, even in the presence of heparin, there is continued growth of thrombus mediated by thrombin bound to fibrin in the pre-existing thrombus. In addition, the doses required to produce an antithrombotic effect are quite unpredictable and, therefore, the dosage must be monitored closely. Low molecular weight heparins (LMWHs) can also be used as anticoagulants and anti-thrombin agents to inhibit fibrin formation, platelet aggregation and thrombus formation. LMWHs act by activating ATIII and, as such, have the same biophysical limitations as heparin. However, LMWHs produce a more predictable anticoagulant effect than heparin. Thus, both heparin and LMWH have the limitation of not readily inactivating surface-bound thrombin. The consequences of this are (a) high concentrations are needed to achieve an anti-thrombin effect which can lead to excessive bleeding, and (b) once the agents are cleared from the circulation, the surface-bound thrombin can reactivate clotting.

Inactivation of clot-bound thrombin may be achieved with another set of compounds known as direct thrombin inhibitors. Such inhibitors include hirudin and its derivatives, and inhibitors of the active site of thrombin, such as argatroban and PACK (D-phenylalanyl-L-propyl-L-arginyl chloromethyl ketone). Hirudin is an anti-thrombin substance extracted from the salivary glands of leeches. Related compounds include hirulog that is a small, synthetic analog of hirudin. While these drugs are able to inhibit clot-bound thrombin, they have the following limitations. First, they do not block thrombin generation because they are selective inhibitors of thrombin. Second, they do not typically inactivate clot-bound thrombin selectively, but do so at the same concentrations that are required to inhibit free thrombin. Thirdly, the inactivation of thrombin is generally stoichiometric and, thus, unless very high concentrations are used, the inhibitory effect can be overcome by the large amounts of thrombin that are generated at sites where surface-bound thrombin accumulates (e.g., on bypass circuits, or at sites of arterial or venous thrombosis). As a result of the above three limitations, high concentrations of direct thrombin inhibitors (e.g., hirudin) must typically be administered to interact with and inhibit the free thrombin generated by clot-bound thrombin. Such high inhibitor concentrations can, however, cause unwanted bleeding. Moreover, direct thrombin inhibitors (e.g., hirudin, its analogs and small molecule active site thrombin inhibitors, such as argatroban) are generally reversible and, thus, the inhibitory effect is lost when the drugs are cleared from the blood. Unfortunately, this reversible inhibition can lead to rebound activation of coagulation.

In view of the foregoing, there remains a need in the art for improved compositions and methods that are useful, for example, for inhibiting thrombogenesis associated with cardiovascular disease. An ideal antithrombotic agent would be one which can pacify the clot by inactivating fibrin-bound thrombin and by blocking thrombin generation, thereby preventing the reactivation of coagulation that occurs once treatment is stopped. The present invention fulfills these and other needs.

SUMMARY OF THE INVENTION

The present invention provides modified low molecular weight heparin (MLMWH) compounds that can pacify the thrombus (or, interchangeably, clot) by inactivating fibrin-bound thrombin, thereby preventing reactivation of coagulation once treatment is stopped, and that can block thrombin generation by inhibiting factor Xa. In addition, the present invention provides methods of using such MLMWH compounds to treat cardiovascular diseases. The MLMWH compounds of the present invention typically have a molecular weight ranging from about 5,000 Daltons to about 9,000 Daltons, more preferably, from about 5,400 Daltons to about 8,000 Daltons and, even more preferably, from about 5,800 Daltons to about 7,000 Daltons. In a presently preferred embodiment, the MLMWH compounds of the present invention have a mean molecular weight of about 6,000 Daltons. Such MLMWH compounds can readily be prepared from low molecular weight heparin (LMWH) or, alternatively, from standard or unfractionated heparin.

Moreover, the MLMWH compounds of the present invention typically have similar anti-factor Xa and anti-factor IIa activities. In a presently preferred embodiment, the ratio of anti-factor Xa activity to anti-factor IIa activity ranges from about 2:1 to about 1:1 and, more preferably, from about 1.5:1 to about 1:1. In contrast, LMWHs, for example, have significantly more anti-factor Xa activity than anti-factor IIa activity. In a presently preferred embodiment, the anti-factor Xa activity of the MLMWH compounds of the present invention ranges from about 90 U/mg to about 150 U/mg and, more preferably, from about 100 U/mg to about 125 U/mg. In an even more preferred embodiment, the MLMWH compounds of the present invention have an anti-factor Xa activity of about 115 U/mg. In a presently preferred embodiment, the anti-factor IIa activity of the MLMWH compounds of the present invention ranges from about 40 U/mg to about 100 U/mg and, more preferably, from about 60 U/mg to about 75 U/mg. In an even more preferred embodiment, the MLMWH compounds of the present invention have an anti-factor IIa activity of about 65 U/mg.

It has been discovered that the heparin chains of the MLMWH compounds of the present invention are too short to bridge thrombin to fibrin, but are of sufficient length to bridge antithrombin to thrombin. Consequently, unlike heparin, the MLMWH compounds of the present invention inactivate both fibrin-bound thrombin and free thrombin. Moreover, although most low molecular weight heparin (LMWH) chains are of insufficient length to bridge thrombin to fibrin, they are also too short to bridge antithrombin to thrombin. Consequently, the MLMWH compounds of the present invention are considerably better than LMWH at inactivating fibrin-bound thrombin. In addition, although hirudin can inactivate fibrin-bound thrombin, it has no effect on thrombin generation because it is a selective inhibitor of thrombin. Consequently, in contrast to hirudin, the MLMWH compounds of the present invention inhibit thrombin generation by catalyzing factor Xa inactivation by antithrombin. Thus, by blocking thrombin generation as well as by inhibiting fibrin-bound thrombin, the MLMWH compounds of the present invention overcome the limitations of heparin, LMWH and hirudin, particularly in the setting of acute arterial thrombosis.

As a result of their ability to (1) inhibit fibrin-bound thrombin as well as fluid-phase thrombin by catalyzing antithrombin, and (2) inhibit thrombin generation by catalyzing factor Xa inactivation by antithrombin, the MLMWH compounds of the present invention can be used to treat cardiovascular diseases, including unstable angina, acute myocardial infarction (heart attack), cerebral vascular accidents (stroke), pulmonary embolism, deep vein thrombosis, arterial thrombosis, etc. As such, the present invention provides methods and pharmaceutical compositions for treating such cardiovascular diseases.

In one embodiment, the present invention provides a method of treating a thrombotic condition in a mammal, the method comprising administering to the mammal a pharmacologically acceptable dose of a MLMWH compound having a molecular weight of about 5,000 Daltons to about 9,000 Daltons, more preferably, of about 5,400 Daltons to about 8,000 Daltons, more preferably, of about 5,800 Daltons to about 7,000 Daltons and, even more preferably, of about 6,000 Daltons. In preferred aspects of this embodiment, the thrombotic condition includes, but is not limited to, venous thrombosis, arterial thrombosis and coronary artery thrombosis. In this embodiment, the MLMWH compound inhibits thrombus formation and growth, for example, by inhibiting fibrin-bound thrombin and fluid-phase thrombin, and by inhibiting thrombin generation by catalyzing factor Xa inactivation by antithrombin. Preferably, administration of the compounds is achieved by parenteral administration (e.g., by intravenous, subcutaneous and intramuscular injection).

In another embodiment, the present invention provides a method of preventing the formation of a thrombus in a mammal at risk of developing thrombosis, the method comprising administering to the mammal a pharmacologically acceptable dose of a MLMWH compound having a molecular weight of about 5,000 Daltons to about 9,000 Daltons, more preferably, of about 5,400 Daltons to about 7,000 Daltons, more preferably, of about 5,800 Daltons to about 6,500 Daltons and, even more preferably, of about 6,000 Daltons. In one aspect of this embodiment, the mammal is at increased risk of developing a thrombus due to a medical condition which disrupts hemostasis (e.g., coronary artery disease, atherosclerosis, etc.). In another aspect of this embodiment, the mammal is at increased risk of developing a thrombus due to a medical procedure (e.g., cardiac surgery (e.g., cardiopulmonary bypass), catheterization (e.g., cardiac catheterization, percutaneous transluminal coronary angioplasty), atherectomy, placement of a prosthetic device (e.g., cardiovascular valve, vascular graft, stent, etc.). In this embodiment, the MLMWH compounds can be administered before, during or after the medical procedure. Moreover, administration of the MLMWH compounds is preferably achieved by parenteral administration (e.g., by intravenous, subcutaneous and intramuscular injection).

Other features, objects and advantages of the invention and its preferred embodiments will become apparent from the detailed description which follows.

DETAILED DESCRIPTION OF THE INVENTION AND PREFERRED EMBODIMENTS

Figure 1:
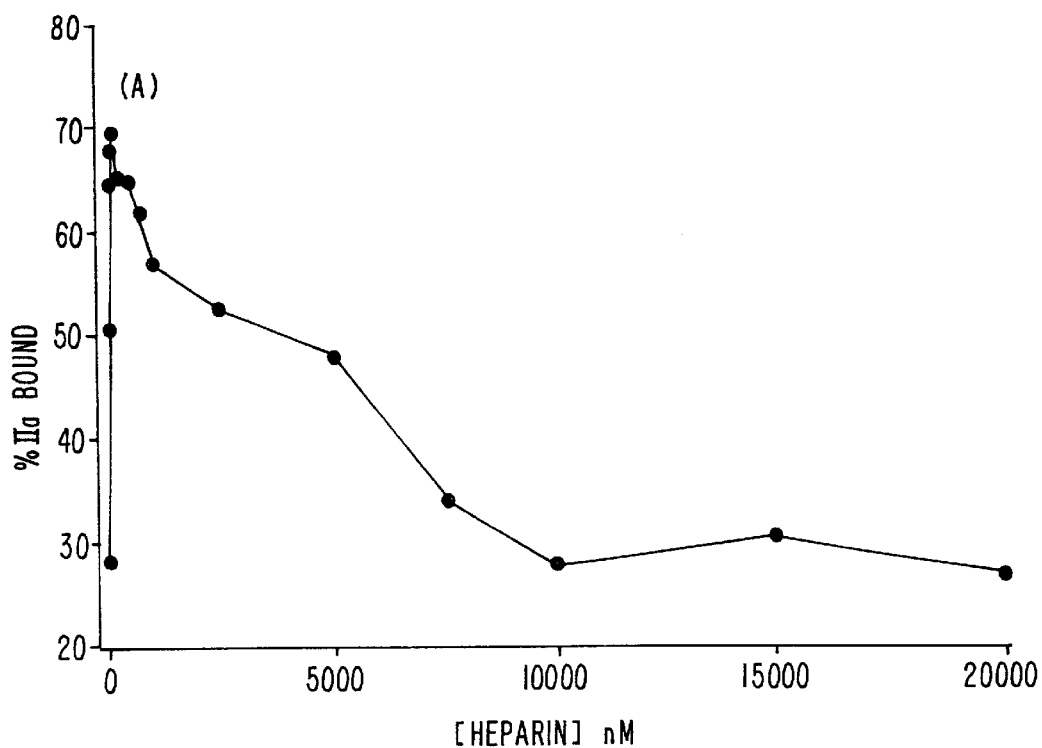
FIGS. 1A and 1B illustrate the effects of varying heparin concentrations on thrombin (IIa) binding to fibrin (A) and on thrombin's apparent affinity for fibrin (B).

The present invention provides modified low molecular weight heparin (MLMWH) compounds that (1) inhibit fibrin-bound thrombin as well as fluid-phase thrombin by catalyzing antithrombin, and (2) inhibit thrombin generation by catalyzing factor Xa inactivation by antithrombin. These MLMWH compounds have a molecular weight ranging from about 5,000 Daltons to about 9,000 Daltons, more preferably, from about 5,400 Daltons to about 8,000 Daltons and, even more preferably, from about 5,800 Daltons to about 7,000 Daltons. In a presently preferred embodiment, the MLMWH compounds of the present invention have a mean molecular weight of about 6,000 Daltons.

More particularly, the MLMWH compounds of the present invention can pacify the intense prothrombotic activity of the thrombus. The prothrombotic activity of the thrombus reflects the activity of fibrin-bound thrombin and platelet-bound activated factor X (factor Xa), both of which are relatively resistant to inactivation by heparin and LMWH. This explains why these agents are of limited efficacy in the setting of arterial thrombosis and why rebound activation of coagulation occurs when treatment is stopped. Moreover, although hirudin can, in contrast to heparin, inactivate fibrin-bound thrombin, it fails to block thrombin generation triggered by platelet-bound factor Xa. The ability of hirudin to inactivate fibrin-bound thrombin explains why direct thrombin inhibitors are superior to heparin for the short-term management of arterial thrombosis. However, any beneficial effects of these agents are rapidly lost once treatment is stopped because they fail to block thrombin generation that is triggered by platelet-bound factor Xa.

It has now been determined that fibrin-bound thrombin is resistant to inactivation by heparin because the heparin bridges thrombin to fibrin by binding to both fibrin and the heparin binding site on thrombin with high affinity; the Kd for both the heparin-fibrin and the heparin-thrombin interaction is about 150 nM. Thrombin within this ternary fibrin-thrombin-heparin complex undergoes a conformational change at its active site that likely limits its reactivity with antithrombin. Furthermore, by occupying the heparin-binding site on thrombin, the heparin chain that tethers thrombin to fibrin prevents heparin within the heparin-antithrombin complex from bridging antithrombin to the fibrin-bound thrombin. This explains why thrombin within the ternary fibrin-thrombin-heparin complex is protected from inactivation by heparin or by LMWH chains that are of sufficient length to bridge thrombin to antithrombin. It is likely that a major contributing factor to both the resistance of acute arterial thrombi to these anticoagulants and rebound activation of coagulation after stopping treatment is the inability of heparin, LMWH or hirudin to pacify the intense prothrombotic activity of the thrombus.

In contrast to heparin, LMWH and hirudin, the MLMWH compounds of the present invention can pacify the prothrombotic activity of the thrombus by inactivating fibrin-bound thrombin and by inhibiting thrombin generation by catalyzing factor Xa inactivation by antithrombin. More particularly, it has been discovered that the heparin chains of the MLMWH compounds of the present invention are too short to bridge thrombin to fibrin, but are of sufficient length to bridge antithrombin to thrombin. Consequently, unlike heparin, the MLMWH compounds of the present invention inactivate both fibrin-bound thrombin and free thrombin. Moreover, although most low molecular weight heparin (LMWH) chains are of insufficient length to bridge thrombin to fibrin, they are also too short to bridge antithrombin to thrombin. Consequently, the MLMWH compounds of the present invention are considerably better than LMWH at inactivating fibrin-bound thrombin. In addition, although hirudin can inactivate fibrin-bound thrombin, it has no effect on thrombin generation because it is a selective inhibitor of thrombin. Consequently, in contrast to hirudin, the MLMWH compounds of the present invention inhibit thrombin generation by catalyzing factor Xa inactivation by antithrombin. Thus, by blocking thrombin generation as well as by inhibiting fibrin-bound thrombin, the MLMWH compounds of the present invention overcome the limitations of heparin, LMWH and hirudin, particularly in the setting of acute arterial thrombosis.

The MLMWH compounds of the present invention typically have similar anti-factor IIa and anti-factor Xa activities. In a presently preferred embodiment, the ratio of anti-factor Xa activity to anti-factor IIa activity ranges from about 2:1 to about 1:1 and, more preferably, from about 1.5:1 to about 1:1. In contrast, LMWHs, for example, have significantly more anti-factor Xa activity than anti-factor IIa activity. In a presently preferred embodiment, the anti-factor Xa activity of the MLMWH compounds of the present invention ranges from about 90 U/mg to about 150 U/mg and, more preferably, from about 100 U/mg to about 125 U/mg. In an even more preferred embodiment, the MLMWH compounds of the present invention have an anti-factor Xa activity of about 115 U/mg. In a presently preferred embodiment, the anti-factor Ia activity of the MLMWH compounds of the present invention ranges from about 40 U/mg to about 100 U/mg and, more preferably, from about 60 U/mg to about 75 U/mg. In an even more preferred embodiment, the MLMWH compounds of the present invention have an anti-factor IIa activity of about 65 U/mg.

The MLMWH compounds of the present invention can be prepared from low molecular weight heparin (LMWH) or, alternatively, from standard or unfractionated heparin. LMWH, as used herein, includes reference to a heparin preparation having an average molecular weight of about 3,000 Daltons to about 8,000 Daltons. Such LMWHs are commercially available from a number of different sources (e.g., SIGMA Chemical Co., St. Louis, Mo.). The MLMWH compounds of the present invention can be prepared from LMWH using a number of different separation or fractionation techniques known to and used by those of skill in the art. Such techniques include, for example, gel permeation chromatography (GPC), high-performance liquid chromatography (HPLC), ultrafiltration, size exclusion chromatography, etc. In a presently preferred embodiment, HPLC is used to isolate or separate out the MLMWH compounds of interest.

More particularly, in one embodiment, a well-defined MLMWH compound having a mean molecular weight of about 6,025 Daltons was separated from LMWH (SIGMA Chemical Company, St. Louis, Mo.) using high-performance liquid chromatography on a Beckman Gold System (Mississauga, Ontario, Canada) equipped with a model 126 solvent delivery system and a manual injector. The fractions were monitored with a Beckman model 167 variable wavelength absorbance detector at 205nm and a Waters model 410 differential refractometer according to the method described by Nielson (Nielson JI, *Thromb. Haemost.*, 68:478–80 (1992)), the teachings of which are incorporated herein by reference. The LMWH was diluted in double deionized water and applied to the column. It was eluted with 0.5M $Na_2SO_4$. The heparin was first eluted from a SEC 3000 gel filtration column, 600×21.2 mm (Phenomenex, Torrance, Calif.). The sample was run at 3 ml/min and samples collected every minute. These samples were subsequently run over a G3000 SWXL TSK column, 30 cm ×7.9 mm (Supelco, Mississauga, Ontario, Canada). This column was also equilibrated in $Na_2SO_4$ and run at flow rate of 0.5 ml/min. Samples were run over this column until the heparin was clean (2 to 3x). Both columns were calibrated using standardized heparin fractions ranging in molecular weight from 1,500 to 17,800 Daltons.

In another embodiment, the MLMWH compounds of the present invention can be obtained from unfractionated heparin by first depolymerizing the unfractionated heparin to yield low molecular weight heparin and then isolating or separating out the MLMWH fraction of interest. Unfractionated heparin is a mixture of polysaccharide chains composed of repeating disaccharides made up of a uronic acid residue (D-glucuronic acid or L-iduronic acid) and a D-glucosamine acid residue. Many of these disaccharides are sulfated on the uronic acid residues and/or the glucosamine residue. Generally, unfractionated heparin has an average molecular weight ranging from about 6,000 Daltons to 40,000 Daltons, depending on the source of the heparin and the methods used to isolate it. The unfractionated heparin used in the process of the present invention can be either a commercial heparin preparation of pharmaceutical quality or a crude heparin preparation, such as is obtained upon extracting active heparin from mammalian tissues or organs. The commercial product (USP heparin) is available from several sources (e.g., SIGMA Chemical Co., St. Louis, Mo.), generally as an alkali metal or alkaline earth salt (most commonly as sodium heparin). Alternatively, the unfractionated heparin can be extracted from mammalian tissues or organs, particularly from intestinal mucosa or lung from, for example, beef, porcine and sheep, using a variety of methods known to those skilled in the art (see, e.g., Coyne, Erwin, *Chemistry and Biology of Heparin*, (Lundblad, R. L., et al. (Eds.), pp. 9–17, Elsevier/North-Holland, New York (1981)). In a presently preferred embodiment, the unfractionated heparin is porcine intestinal heparin.

Numerous processes for the depolymerization of heparin are known and have been extensively reported in both the scientific and patent literature, and are applicable to the present invention. Such processes are generally based on either chemical or enzymatic reactions. For instance, LMWH can be prepared from standard, unfractionated heparin by benzylation followed by alkaline depolymerization; nitrous acid depolymerization; enzymatic depolymerization with heparinase; peroxidative depolymerization, etc. In a presently preferred embodiment, LMWH is prepared from unfractionated heparin using nitrous acid depolymerization.

The unfractionated heparin is depolymerized by contacting unfractionated heparin, under controlled conditions, to the actions of a chemical agent, more particularly, nitrous acid. The nitrous acid can be added to the heparin directly or, alternatively, it can be formed in situ. To generate the nitrous acid in situ, controlled amounts of an acid are added to a derivative of nitrous acid. Suitable acids include those which advantageously contain biologically acceptable anions, such as acetic acid and, more preferably, hydrochloric acid. Suitable derivatives of nitrous acid include a salt, an ether-salt or, more preferably, an alkali or alkaline-earth salt. In a presently preferred embodiment, a salt of nitrous acid, a water-soluble salt, more preferably, an alkali salt, such as sodium nitrite ($NaNO_2$), is used.

The depolymerization of unfractionated heparin is preferably carried out in a physiologically acceptable medium, thereby eliminating the problems associated with the use of a solvent that can be detrimental to the contemplated biological applications. Such physiologically acceptable media include, but are not limited to, water and water/alcohol mixtures. In a presently preferred embodiment, water constitutes the preferred reaction medium. In carrying out the depolymerization reaction, it is desirable to use stoichiometric amounts of the reagents (e.g., nitrous acid). The use of stoichiometric amounts of nitrous acid will ensure that when the desired degree of depolymerization is reached, the nitrous acid is entirely consumed. Typically, the weight ratio of unfractionated heparin to sodium nitrite ($NaNO_2$) ranges from about 100 to 2–4 and, more preferably, from about 100 to 3. Using a stoichiometric amount of nitrous acid avoids the need to "quench" a kinetic (ongoing) reaction with, for example, ammonium sulfamate and, in turn, prevents the formation of mixed salts (e.g., sodium and ammonium) of the LMWH intermediates.

In addition, other parameters, such as temperature and pH, are adjusted with respect to one another in order to obtain the desired products under the most satisfactory experimental conditions. For instance, the depolymerization reaction can be carried out at temperatures ranging from about 0° to 30° C. In fact, temperatures lower than 10° C. can be used for the production of the desired products. However, in a preferred embodiment, the depolymerization reaction is carried out at ambient temperature, i.e., between about 20° C. and 28° C. Moreover, in a preferred embodiment, the depolymerization reaction is initiated and terminated by first lowering and then raising the pH of the reaction mixture. To initiate the depolymerization reaction, the pH of the reaction mixture is lowered to a pH of about 2.5 to 3.5 and, more preferably, to a pH of about 3.0. Similarly, to terminate the depolymerization reaction, the pH of the reaction mixture is raised to a pH of about 6.0 to 7.0 and, more preferably, to a pH of about 6.75. It should be noted that the progress of the reaction can be monitored by checking for the presence or absence of nitrous ions in the reaction mixture using, for example, starch-iodine paper. The absence of nitrous ions in the reaction mixture indicates that the reaction has gone to completion. The time required for the reaction to reach completion will vary depending on the reactants and reaction conditions employed. Typically, however, the reaction will reach completion in anywhere from about 1 hr to about 3 hr.

Once the reaction has reached completion, the LMWH can be recovered using a number of different techniques known to and used by those of skill in the art. In one embodiment, the LMWH is recovered from the reaction mixture by precipitation, ultrafiltration or chromatography methods. If the desired product is obtained by precipitation, this is generally done using, for example, an alcohol (e.g., absolute ethanol). In a presently preferred embodiment, the low molecular weight heparin is recovered from the reaction mixture using ultrafiltration methods. Ultrafiltration membranes of various molecular weight cuts-offs can advantageously be used to both desalt and define the molecular weight characteristics of the resulting LMWH.

Ultrafiltration systems suitable for use in accordance with the present invention are known to and used by those of skill in the art. The commercially available Millipore Pellicon ultrafiltration device is an exemplary ultrafiltration system that can be used in accordance with the present invention. This device can be equipped with various molecular weight cut-off membranes. In a presently preferred embodiment, the resulting LMWH is dialyzed or ultrafiltered against purified water (i.e., distilled water ($dH_2 0$)) using a Millipore Pellicon ultrafiltration device equipped with 3,000 Dalton molecular weight cut-off membranes.

After ultrafiltration, the retentate is then lyophilized, i.e., freeze-dried, to give LMWH. The molecular weight characteristics of the resulting LMWH can be determined using standard techniques known to and used by those of skill in the art. Such techniques include, for example, GPC-HPLC, viscosity measurements, light scattering, chemical or physical-chemical determination of functional groups created during the depolymerization process, etc. In a preferred embodiment, the molecular weight characteristics of the resulting LMWH are determined by high performance size exclusion chromatography in conjunction with multiangle laser light scattering (HPSEC-MALLS). Typically, the resulting LMWH has a molecular weight average (Mw) of between about 3,000 to about 8,000 Daltons. Thereafter, the MLMWH compounds of the present invention are obtained from the resulting LMWH fraction using the separation techniques described above.

Those of skill in the art will readily appreciate that the resulting MLMWH compounds can be subjected to further purification procedures. Such procedures include, but are not limited to, gel permeation chromatography, ultrafiltration, hydrophobic interaction chromatography, affinity chromatography, ion exchange chromatography, etc.

Moreover, the molecular weight characteristics of the MLMWH compounds of the present invention can be determined using standard techniques known to and used by those of skill in the art as described above. In a preferred embodiment, the molecular weight characteristics of the MLMWH compounds of the present invention are determined by high performance size exclusion chromatography in conjunction with multiangle laser light scattering (HPSEC-MALLS).

In another embodiment, the MLMWH compounds of the present invention can be obtained by a limited periodate oxidation/hydrolysis of heparin to yield low molecular weight heparin and then isolating or separating out the MLMWH fraction of interest. In the first step of this method, heparin is contacted with a limited amount of sodium periodate. In a presently preferred embodiment, the concentration of sodium periodate ranges from about 1 mM to about 50 mM and, more preferably, from about 5mM to 20 mM. The pH of this reaction mixture ranges from about 3 to 11 and, more preferably, from about 6.5 to about 7.5. The limited periodate oxidation is generally carried out for about 18 hours. In the second step of this method, an alkaline hydrolysis is carried out after the periodate oxidation using metal alkalines, such as NaOH. In a presently preferred embodiment, the concentration of the metal alkaline, e.g., NaOH, ranges from about 0.1 N to about 1N and, more preferably, is about 0.25 N. This step is carried out at a temperature ranging from about 0° C. to about 50° C. and, more preferably, at a temperature of about 25° C., for a time period of about 1 hour to about 10 hours and, more preferably, 3 hours. The desired MLMWH compounds are obtained using known methods, such as gel-filtration, ion-exchange chromatography, ultrafiltration, dialysis, quaternary ammonium precipitation, and organic solvent precipitation, as described above. Moreover, the MLMWH compounds can be further purified using the methods described above.

The MLMWH compounds of the present invention are capable of, inter alia, (1) inhibiting fibrin-bound thrombin as well as fluid-phase thrombin by catalyzing antithrombin, and (2) inhibiting thrombin generation by catalyzing factor Xa inactivation by antithrombin. As such, the MLMWH compounds of the present invention can be used to treat a number of important cardiovascular complications, including unstable angina, acute myocardial infarction (heart attack), cerebral vascular accidents (stroke), pulmonary embolism, deep vein thrombosis, arterial thrombosis, etc. In a presently preferred embodiment, the MLMWH compounds of the present invention are used to treat arterial thrombosis. As such, in another embodiment, the MLMWH compounds of the present invention can be incorporated as components in pharmaceutical compositions that are useful for treating such cardiovascular conditions. The pharmaceutical compositions of the present invention are useful either alone or in conjunction with conventional thrombolytic treatments, such as the administration of tissue plasminogen activator (tPA), streptokinase, and the like, with conventional anti-platelet treatments, such as the administration of ticlopidine, and the like, as well as with intravascular intervention, such as angioplasty, atherectomy, and the like.

The MLMWH compounds of this invention can be incorporated into a variety of formulations for therapeutic administration. More particularly, the MLMWH compounds of the present invention can be formulated into pharmaceutical compositions by combination with appropriate, pharmaceutically acceptable carriers or diluents, and may be formulated into various preparations, preferably in liquid forms, such as slurries, solutions and injections. Administration of the MLMWH compounds of the present invention is preferably achieved by parenteral administration (e.g., by intravenous, subcutaneous and intramuscular injection). Moreover, the compounds can be administered in a local rather than systemic manner, for example via injection of the compounds directly into a subcutaneous site, often in a depot or sustained release formulation.

Suitable formulations for use in the present invention are found in *Remington's Pharmaceutical Sciences* (Mack Publishing Company, Philadelphia, Pa., 17th ed. (1985)), the teachings of which are incorporated herein by reference.

Moreover, for a brief review of methods for drug delivery, see, Langer, *Science* 249:1527–1533 (1990), the teachings of which are incorporated herein by reference. The pharmaceutical compositions described herein can be manufactured in a manner that is known to those of skill in the art, i.e., by means of conventional mixing, dissolving, levigating, emulsifying, entrapping or lyophilizing processes. The following methods and excipients are merely exemplary and are in no way limiting.

The MLMWH compounds of the present inventions are preferably formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

Generally, pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes.

Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

More particularly, for injection, the MLMWH compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives, such as solubilizers, isotonic agents, suspending agents, emulsifying agents, stabilizers and preservatives. Preferably, the compounds of the invention may be formulated in aqueous solutions, preferably in physiologically compatible buffers, such as Hanks's solution, Ringer's solution, or physiological saline buffer.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Pharmaceutical compositions suitable for use in the present invention include compositions wherein the active ingredients are contained in a therapeutically effective amount. By a "therapeutically effective amount" or, interchangeably, "pharmacologically acceptable dose" or, interchangeably, "anticoagulantly effective amount," it is meant that a sufficient amount of the compound, i.e., the MLMWH compound, will be present in order to achieve a desired result, e.g., inhibition of thrombus accretion when treating a thrombus-related cardiovascular condition, such as those described above by, for example, inactivating clot-bound thrombin, inhibiting thrombin generation by catalyzing factor Xa inactivation by antithrombin, etc. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

Typically, the active product, i.e., the MLMWH compounds, will be present in the pharmaceutical composition at a concentration ranging from about 2 $\mu$g per dose to 200 $\mu$g per dose and, more preferably, at a concentration ranging from about 5 $\mu$g per dose to 50 $\mu$g per dose. Daily dosages can vary widely, depending on the specific activity of the particular MLMWH, but will usually be present at a concentration ranging from about 0.5 μg per kg of body weight per day to about 15 μg per kg of body weight per day and, more preferably, at a concentration ranging from about 1 μg per kg of body weight per day to about 5 μg per kg of body weight per day.

In addition to being useful in pharmaceutical compositions for the treatment of the cardiovascular conditions described above, one of skill in the art will readily appreciate that the active products, i.e., the MLMWH compounds, can be used as reagents for elucidating the mechanism of blood coagulation in vitro.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

A. Preparation of Modified Low Molecular Weight Heparin (MLMWH)

A well-defined heparin 6,025 Da molecular weight compound was separated from low molecular weight heparin (LMWH) (Sigma Chemical Company, St. Louis, Mo.) by high-performance liquid chromatography on a Beckman Gold System (Mississauga, Ontario Canada) equipped with a model 126 solvent delivery system and a manual injector. The fractions were monitored with a Beckman model 167 variable wavelength absorbance detector at 205 nm and a Waters model 410 differential refractometer according to the method described by Nielsen (1992). The LMWH heparin was diluted in double deionized water and applied to the column. It was eluted with 0.5M $Na_2SO_4$. The heparin was first eluted from a SEC 3000 gel filtration column, 600×21.2 mm purchased from Phenomenex, Torrance, Calif. The sample was run at 3 ml/min and samples collected every minute. These samples were subsequently run over a G3000 SWXL TSK column, 30 cm×7.9 mm from Supelco (Mississauga, Ont.) This column was also equilibrated in $Na_2SO_4$ and run at flow rate of 0.5 nil/min. Samples were run over this column until the heparin was clean (2 to 3×). Both columns were calibrated using standardized heparin fractions ranging in molecular weight from 1,500 to 17,800.

B. Experimental Finding 1.1 Clinical Limitations of Currently Available Anticoagulants:

Heparin, LMWH and direct thrombin inhibitors have limitations in acute coronary syndromes. In patients with unstable angina, there is a clustering of recurrent ischemic events after treatment with these agents is stopped (Theroux, P., et al. (1992) *N. Engl. J. Med.* 327:141–145; Granger, C. B., et al. (1996) *Circulation* 93:870–888; Oldgren, J., et al. (1996) *Circulation* 94 (supply 1):1431). This is due to reactivation of coagulation because there is an associated elevation in plasma levels of prothrombin fragments F1.2 (F1.2) and fibrinopeptide A (FPA), reflecting increased thrombin generation and thrombin activity, respectively (Granger, C. B., et al. (1995) *Circulation* 91:1929–1935). In patients with acute myocardial infarction, thrombolytic therapy with tissue plasminogen activator (t-PA) or streptokinase induces a procoagulant state characterized by elevated levels of FPA (Eisenberg, P. R., et al. (1987) *J. Am. Coll. Cardiol.* 10:527–529; Owen, J., et al. (1988) *Blood* 72:616–620), which are only partially reduced by heparin (Galvani, J., et al. (1994) *J. Am. Coll. Cardiol.* 24:1445–1452; Merlini, P. A., et al. (1995) *J. Am. Coll. Cardiol.* 25:203–209). This explains why adjunctive heparin does not reduce the incidence of recurrent ischemic events in patients receiving streptokinase (Collins, R., et al. (1996) *BMJ* 313:652–659), and is of only questionable benefit in those given t-PA (Collins, R., et al. (1996) *BMJ* 313:652–659). Although hirudin is better than heparin both as an adjunct to thrombolytic therapy and in patients with non-Q wave infarction who do not receive thrombolytic agents, the early benefits of hirudin are lost within 30 days (GUSTO Investigators (1996) *N. Engl. J. Med.* 335(11):775–782). These findings suggest that there is a persistent thrombogenic stimulus that is resistant to both heparin and hirudin.

Similar results are seen in the setting of coronary angioplasty. Recurrent ischemic events occur in 6–8% of patients despite aspirin and high-dose heparin (Popma, J. J., et al. (1995) *Chest* 108:486–501). Although hirudin is superior to heparin for the first 72 hours after successful coronary angioplasty, its benefits are lost by 30 days (Serruys, P. W., et al. (1995) *N. Engl. J. Med.* 333:757–763). Similarly, at 7 days, hirulog, a semi-synthetic hirudin analogue (Bittl, J. A., et al. (1995) *J. Med.* 333:764–769), is better than heparin at preventing recurrent ischemic events in patients undergoing angioplasty for unstable angina after acute myocardial infarction; by 30 days, however, there is no difference between hirulog and heparin (Bittl, J. A., et al. (1995) *J. Med.* 333:764–769). It is likely that both the resistance of acute arterial thrombi to heparin, LMWH and hirudin and the reactivation of coagulation that occurs when treatment is stopped reflect the inability of these anticoagulants to pacify the intense prothrombotic activity of the thrombus.

1.2 Factors Responsible for the Prothrombotic Activity of Acute Arterial Thrombi:

Arterial thrombosis is triggered by vascular injury. Spontaneous or traumatic rupture of atherosclerotic plaque exposes tissue factor which complexes factor VII/VIIa. The factor VIIa/tissue factor complex then initiates coagulation by activating factors IX and X. Although factor VIIa within the factor VIIa/tissue factor complex is rapidly inactivated by tissue factor pathway inhibitor (Broze G J Jr. (1995) *Thromb. Haemost.* 74:90–93), arterial thrombi remain thrombogenic.

Studies in vitro have attributed the procoagulant activity of arterial thrombi to (a) thrombin bound to fibrin (Hogg, P. J., et al. (1989) *Proc. Natl. Acad. Sci. USA* 86:36193623; Weitz, J. I., et al. (1990) *J. Clin. Invest.* 86:385–391), or (b) factor Xa (and possibly factor IXa) bound to platelets within the thrombi (Eisenberg, P. R., et al. (1993) *J. Clin. Invest.* 91:1877–1883). Fibrin-bound thrombin can locally activate platelets (Kumar, R., et al. (1995) *Thromb. Haemost.* 74(3):962–968) and accelerate coagulation (Kumar, R., et al. (1994) *Thromb. Haemost.* 72:713–721), thereby inducing an intense procoagulant state. By triggering thrombin generation, platelet-bound factor Xa (and IXa) augments this procoagulant state.

Both fibrin-bound thrombin and platelet-bound factor Xa are resistant to inactivation by heparin and LMWH (Hogg, P. J., et al. (1989) *Proc. Natl. Acad. Sci. USA* 86:36193623; Weitz, J. I., et al. (1990) *J. Clin. Invest.* 86:385–391; Teitel, J.M., et al. (1983) *J. Clin. Invest.* 71:1383–1391; Pieters, J., et al. (1988) *J. Biol. Chem.* 263:15313–15318), thereby explaining their inability to pacify the procoagulant activity of acute arterial thrombi. Hirudin can inactivate fibrin-bound thrombin (Weitz, J. I., et al. (1990) *J. Clin. Invest.* 86:385–391), but fails to block thrombin generation triggered by platelet-bound clotting factors. In support of this concept, hirudin reduces the levels of FPA, but has no effect on F1.2 levels in patients with unstable angina (Granger, C. B., et al. (1995) *Circulation* 91:1929–1935).

There is mounting evidence that both fibrin-bound thrombin and platelet-bound factor Xa contribute to the intense procoagulant activity of thrombi. Thus, the ability of a washed plasma clot to accelerate coagulation when incubated in unanticoagulated whole blood cannot be blocked by either hirudin or tick anticoagulant peptide (TAP), a direct inhibitor of factor Xa that unlike heparin and LMWH inactivates platelet-bound factor Xa as well as free factor Xa (Waxman, L., et al. (1990) Science248:593–596). In contrast, a combination of hirudin and TAP abolishes the procoagulant activity of plasma clots, suggesting that pacification of acute arterial thrombi requires agents that not only inhibit fibrin-bound thrombin, but also block thrombin generation triggered by platelet-bound factor Xa. Development of these agents requires an understanding of the mechanisms by which fibrin-bound IIa and platelet-bound factor Xa are protected from inactivation by heparin, LMWH and hirudin.

1.3 Mechanisms by Which Fibrin-bound Thrombin is Protected from Inactivation by Heparin:

Studies indicate that thrombin binding to fibrin is more complex in the presence of heparin than in its absence, and the consequence of thrombin/fibrin interactions has now been better delineated.

1.3.1 Thrombin/Fibrin Interactions in the Absence of Heparin:

In the absence of heparin, α-thrombin binds to fibrin with a Kd =2 μM. Binding is mediated by exosite 1, the substrate-binding site on thrombin (Fenton, J. W. II, et al. (1988) Biochemistry 27:7106–7112) because γ-thrombin (a degraded form of thrombin in which exosite 1 is cleaved) and Quick 1 dysthrombin (a naturally occurring thrombin mutant with Arg 67 within exosite 1 replaced by Cys) fail to bind, whereas RA-thrombin (an exosite 2 mutant (Ye, J., et al. (1994) J. Biol. Chem. 269:17965–17970) with decreased affinity for heparin because Arg residues 93, 97, and 101 are replaced by Ala) binds to fibrin with an affinity similar to that of α-thrombin.

1.3.2 Thrombin/Fibrin Interactions in the Presence of Heparin:

When heparin is present, the amount of thrombin that binds to fibrin changes, as does the mode of thrombin interaction with fibrin. With heparin concentrations up to 250 nM, the amount of thrombin that binds to fibrin increases (FIG. 1A) as does the apparent affinity of thrombin for fibrin (FIG. 1B); at higher heparin concentrations, however, thrombin binding (FIG. 1A) and the affinity of thrombin for fibrin progressively decrease (FIG. 1B). These data extend the results of Hogg and Jackson who demonstrated enhanced thrombin binding to fibrin with fixed concentrations of heparin (see, Hogg, P. J., et al., J. Biol. Chem. 265:241-247 (1990)).

Figure 2:
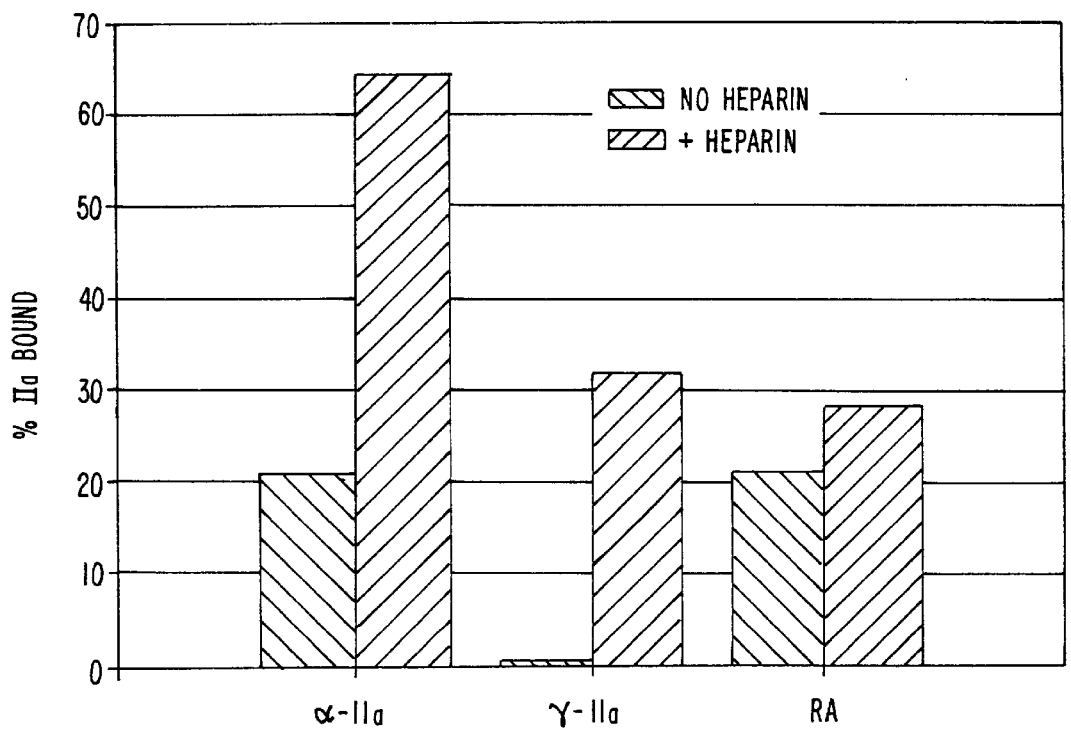
FIG. 2 illustrates the percentage of α-thrombin (α-IIa), γ-thrombin (γIIa) or RA-thrombin (RA) that binds to fibrin monomer-sepharose in the absence or presence of heparin.
Figure 3:
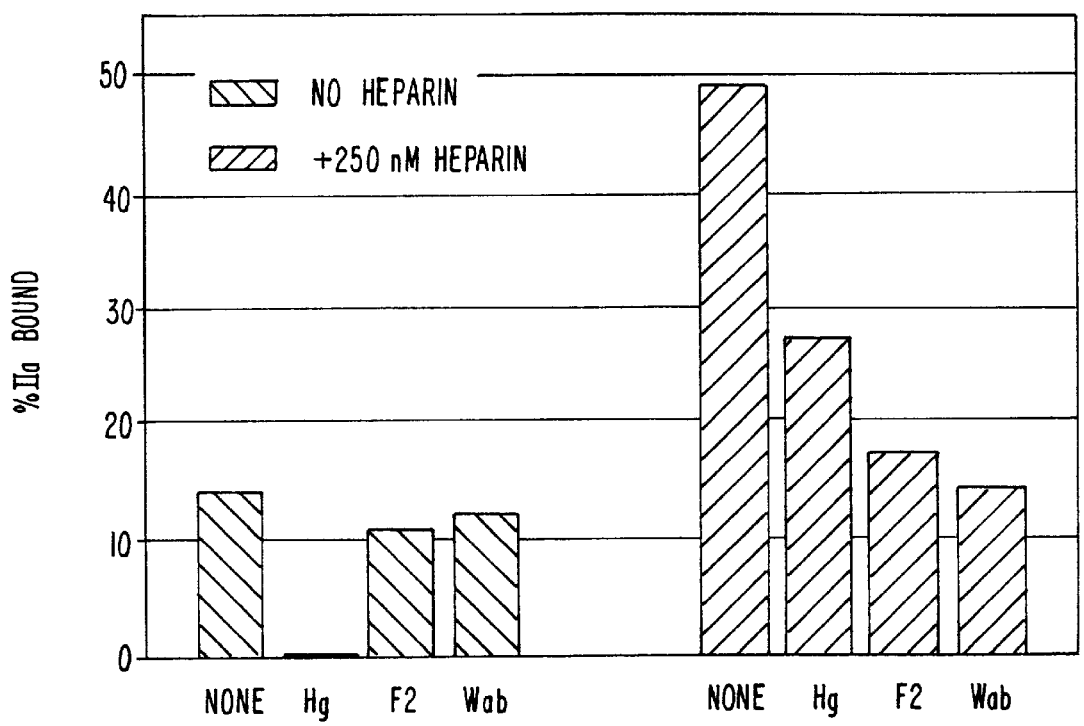
FIG. 3 illustrates the effect of hirugen (Hg), prothrombin fragment 2 (F2) or antibody against exosite 2 (Wab) on thrombin (IIa) binding to fibrin monomersepharose in the absence or presence of 250 nM heparin.

The mode of thrombin binding also changes in the presence of heparin. Whereas thrombin binds to fibrin via exosite 1 in the absence of heparin, enhanced α-thrombin binding seen in the presence of heparin is mediated by exosite 2 because heparin augments the binding of γ-thrombin to the same extent as α-thrombin but has little effect on the binding of RA-thrombin (FIG. 2). Furthermore, excess α-thrombin bound in the presence of heparin is displaced with an antibody to exosite 2 or with prothrombin fragment 2 (F2) which, like heparin, also binds to exosite 2 (Arni, R. K., et al. (1993) Biochemistry 32:4727–4737). In contrast, hirugen, a synthetic analogue of the C-terminal of hirudin (Maraganore, J., et al. (1989) J. Biol. Chem. 264:8692–8698), has no effect on heparin-dependent binding of thrombin (FIG. 3).

Figure 4:
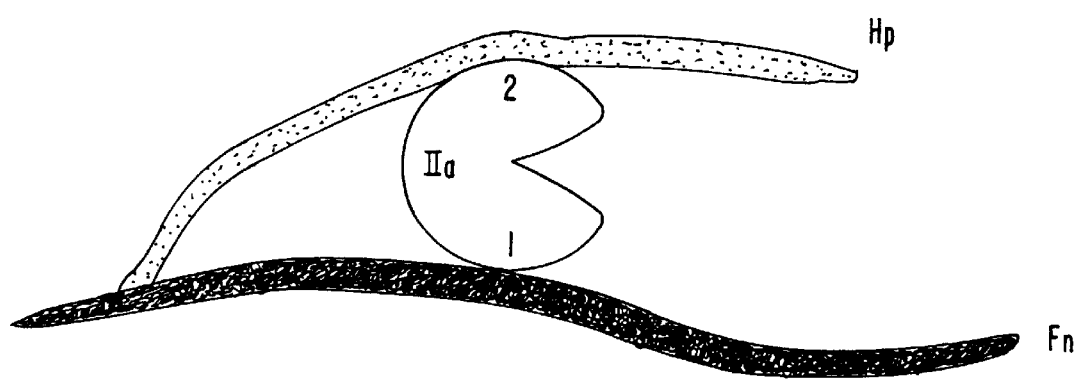
FIG. 4 illustrates the ternary fibrin-thrombin-heparin complex wherein thrombin (IIa) binds to fibrin (Fn) via exosite 1 and heparin (Hp) binds to both Fn and exosite 2 on IIa.

Such findings are interpreted as indicating ternary fibrin-thrombin-heparin complex formation wherein thrombin binds to fibrin directly via exosite 1, and heparin binds to both fibrin and exosite 2 on thrombin (FIG. 4). This occurs because the affinity of heparin for fibrin (Kd=180 nM) is similar to its affinity for α-thrombin (Kd=120 nM). Heparin's interaction with fibrin is pentasaccharide-independent because heparin chains with low affinity for antithrombin bind as tightly as high affinity chains. The biphasic effect of heparin on thrombin binding (FIG. 1) supports the concept of ternary complex formation. Thus, heparin promotes thrombin binding to fibrin until the heparin binding sites are saturated. With higher heparin concentrations, thrombin binding decreases as nonproductive binary fibrin-heparin and thrombin-heparin complexes are formed.

Figure 5:
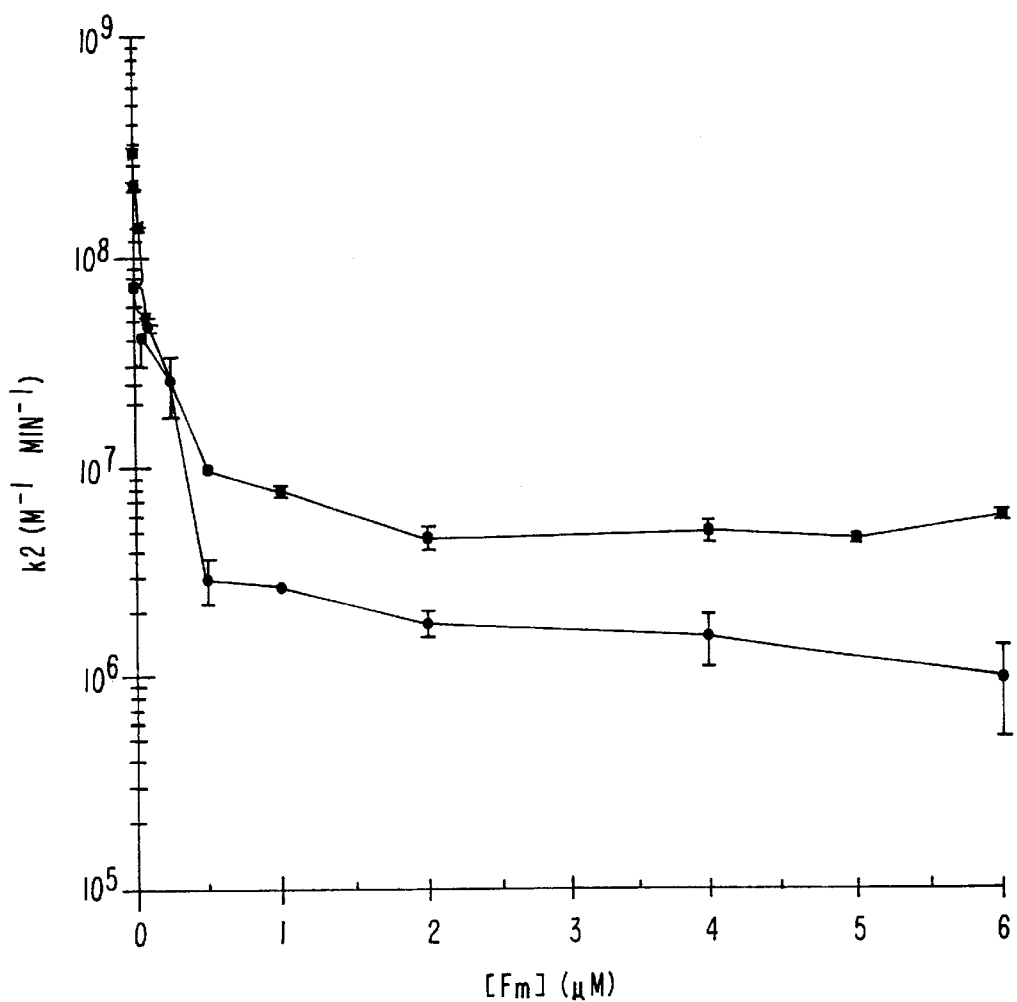
FIG. 5 illustrates the effect of fibrin monomer (Fm) on the rates of thrombin inhibition by antithrombin (■) or heparin cofactor II (●) in the presence of 100 nM heparin. Each point represents the mean of at least 2 separate experiments, while the bars represent the SD.
Figure 6A:
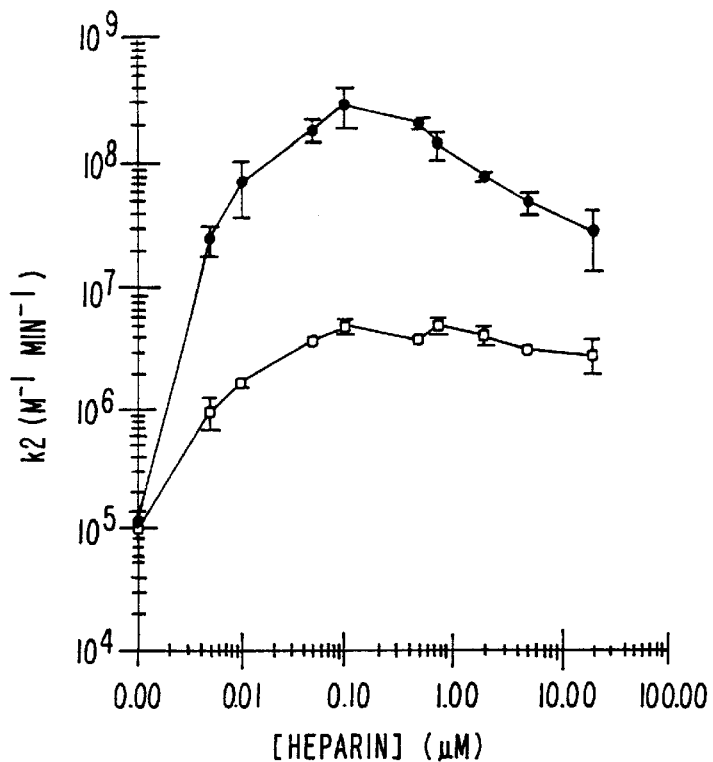
FIGS. 6A and 6B illustrate the inhibitory effects of 4 µM fibrin monomer (□) on the rates of thrombin inhibition by antithrombin (A) or heparin cofactor II (B) in the absence or presence of heparin at the concentrations indicated. Each point represents the mean of at least 2 experiments, while the bars represent the SD.
Figure 6B:
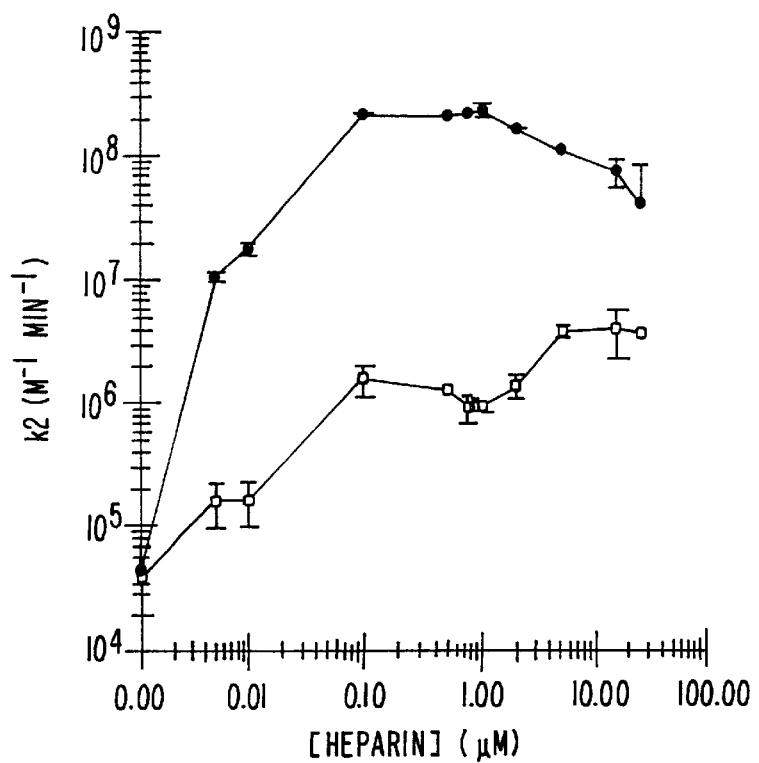
Figure 7:
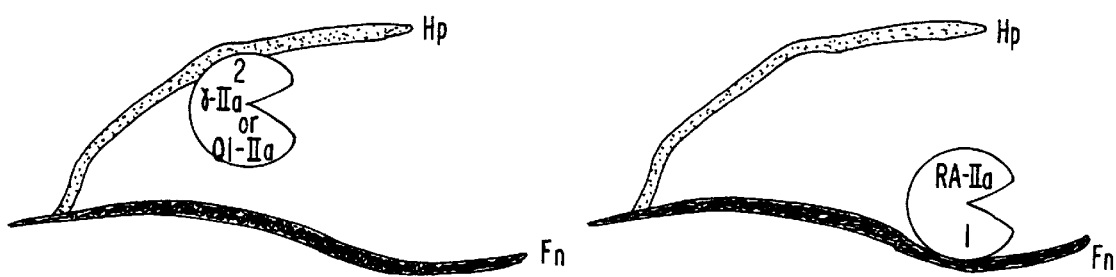
FIG. 7 illustrates the interaction of γ-thrombin (γ-IIa), Quick 1 dysthrombin (Q1-IIa) or RA-IIa with fibrin (Fn) in the presence of heparin (Hp). Non-productive ternary complexes are formed because γ-IIa and Q1-IIa have an altered exosite 1, whereas RA-IIa has reduced affinity for Hp.

1.3.3 Consequences of Thrombin/Fibrin Interactions:

Thrombin within the ternary fibrin-thrombin-heparin complex is protected from inactivation by both antithrombin and heparin cofactor II (HCII). HCII is a naturally occurring antithrombin found in plasma that serves as a secondary inhibitor of thrombin. Thus, the heparin-catalyzed rate of thrombin inactivation by antithrombin or HCII is decreased in the presence of fibrin monomer (FIG. 5). Over a wide range of heparin concentrations, the rates of inactivation by antithrombin and HCII in the presence of saturating amounts of fibrin monomer are up to 60- and 250-fold slower, respectively, than they are in its absence (FIGS. 6A and 6B). For protection to occur, both exosites must be occupied; exosite 1 by fibrin and exosite 2 by heparin. Thus, even though heparin enhances the binding of γ-thrombin and Quick 1 dysthrombin to fibrin by binding to their intact exosite 2 and bridging them to fibrin, neither is protected from inactivation because their altered exosite 1 fails to interact with fibrin (FIG. 7). RA-thrombin is susceptible to inactivation because even though it binds to fibrin with an affinity similar to that of α-thrombin, it has reduced affinity for heparin because of mutations at exosite 2 (FIG. 7).

Figure 8:
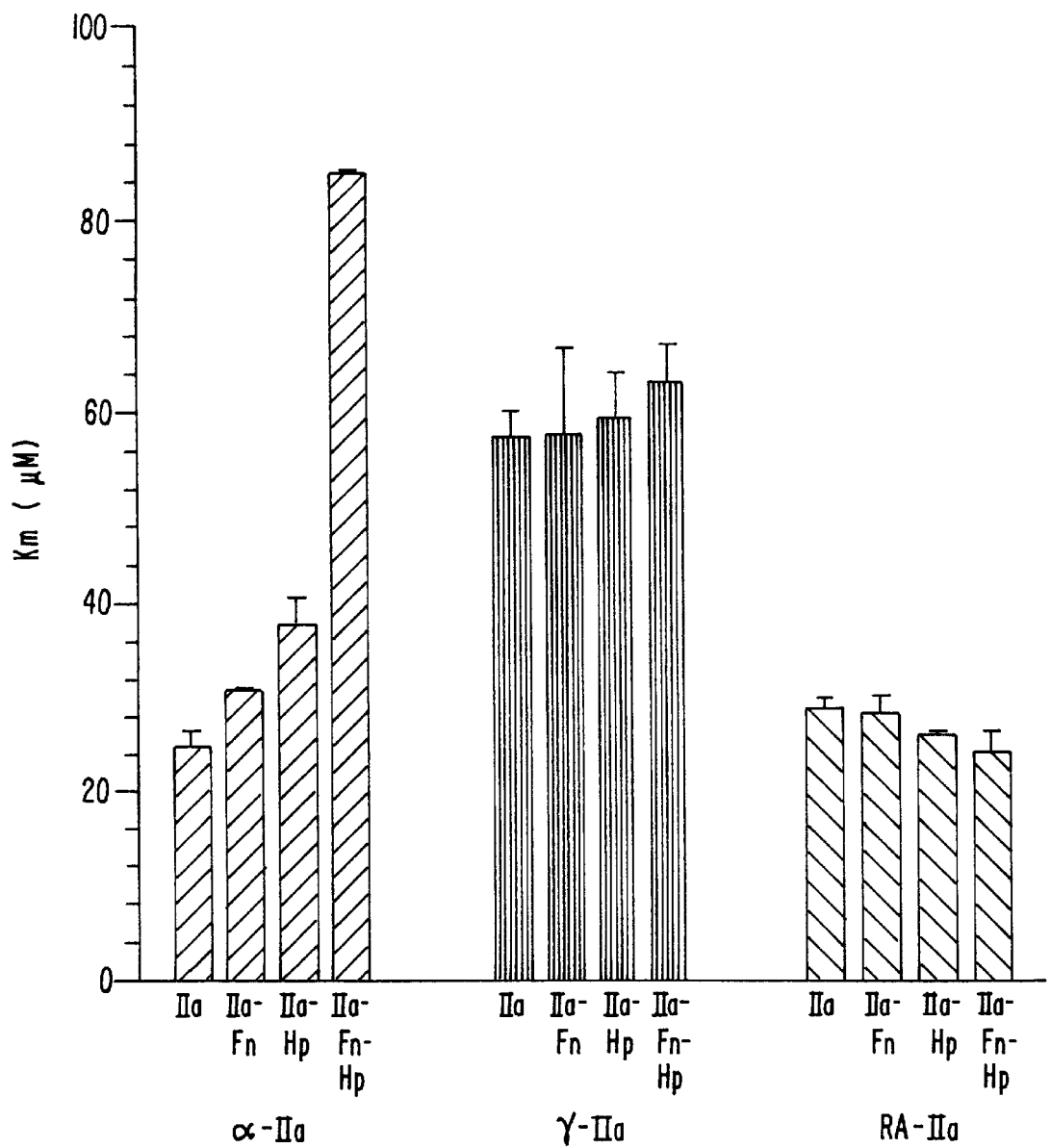
FIG. 8 illustrates the effect of binary or ternary complex formation on the Km for hydrolysis of N-p-Tosyl-Gly-Pro-Arg-p-nitroanilide by α-thrombin (α-IIa),γ-thrombin (γ-IIa), or RA-thrombin (RA-IIa). Binary complexes include thrombin-fibrin (IIa-Fn), and thrombin-heparin (IIa-Hp), whereas the ternary complex is thrombin-fibrin-heparin (IIa-Fn-Hp). Each bar represents the mean of at least two experiments, while the lines represent the SD.

1.3.4 Evidence that Thrombin Within the Ternary Fibrin-Thrombin-Heparin Complex Undergoes Allosteric Changes at the Active Site:

Allosteric changes in the active site of thrombin induced by ternary complex formation likely reduce thrombin reactivity with its substrates or inhibitors. In support of this concept, it has been shown that the rate of thrombin-mediated cleavage of a synthetic substrate is increased when IIa is bound within the ternary fibrin-thrombin-heparin complex, but not with binary thrombin-heparin or thrombin-fibrin complexes (FIG. 8).

2.0 Development of Modified Low Molecular Weight Heparin:

To catalyze thrombin inhibition, heparin bridges antithrombin to thrombin (Danielsson, A., et al. (1986) J. Biol. Chem. 261:15467–15473). Provision of this bridging function requires heparin chains with a minimal molecular weight of 5,400 (Jordan, R. E., et al. (1980) J. Biol. Chem. 225:10081–10090). Because the majority of LMWH molecules are <5,400 Da, LMWH has little inhibitory activity against thrombin (Jordan, R. E., et al. (1980) J. Biol. Chem. 225:10081–10090). Since heparin bridges thrombin to fibrin to form the ternary fibrin-thrombin-heparin complex, it was hypothesized that this function also requires heparin chains of minimum molecular mass. Further, it was postulated that if this minimum molecular mass is different from that needed to bridge antithrombin to thrombin, there may be a window wherein the heparin chains are too short to bridge thrombin to fibrin, but are of sufficient length to bridge antithrombin to thrombin, thereby overcoming an important mechanism of heparin resistance.

Figure 9:
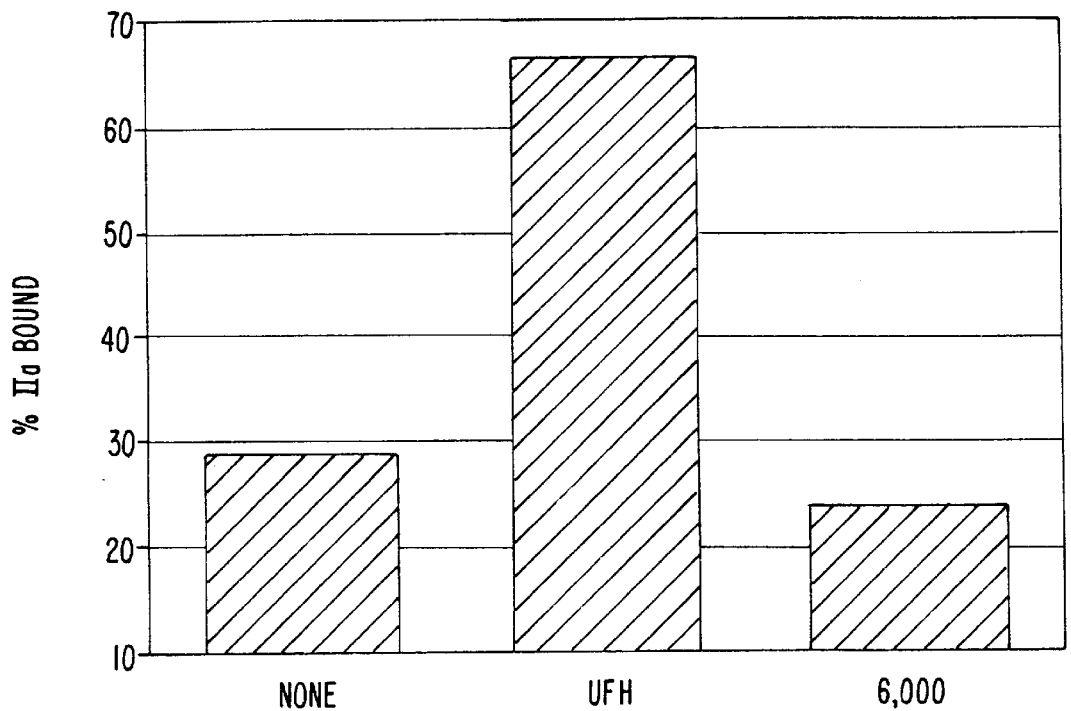
FIG. 9 illustrates the effect of unfractionated heparin (UFH) and a 6,000 Da heparin fraction (MLMWH) on thrombin (IIa) binding to fibrin.
Figure 10:
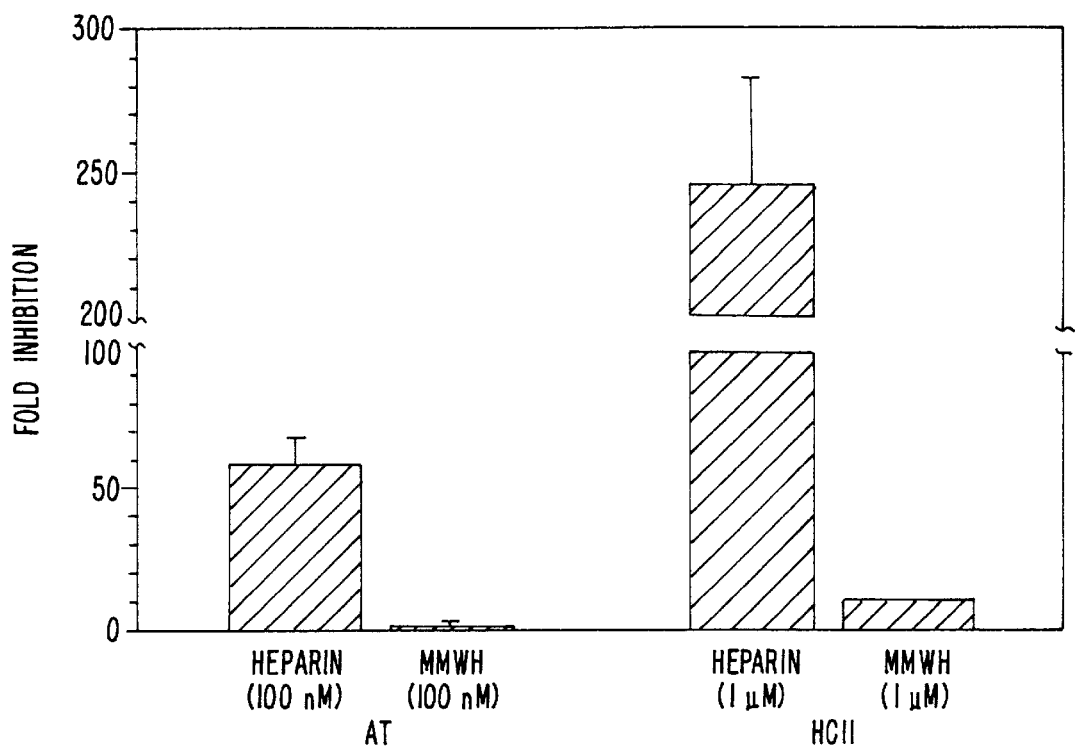
FIG. 10 illustrates the inhibitory effects of 4 µM fibrin monomer on the rate of thrombin inhibition by antithrombin (AT) or heparin cofactor II (HCII) in the presence of heparin or a 6000 Da heparin fraction (MLMWH). Each bar represents the mean of at least 2 separate experiments, while the lines represent the SD.

It has now been discovered that such a window exists. For instance, V21, one of the MLMWH compounds of the present invention with a molecular mass narrowly restricted to 6,000 Da, is long enough to catalyze thrombin inhibition by antithrombin but does not promote thrombin binding to fibrin (FIG. 9). In contrast to heparin, therefore, the rate of MLMWH-catalyzed thrombin inhibition by antithrombin or HCII is almost the same in the presence of fibrin as it is in its absence (FIG. 10).

2.1 Characteristics of Modified Low Molecular Weight Heparin:

Because the chains of MLMWH are of sufficient length to bridge antithrombin to thrombin, the anti-factor IIa (i.e., the ability of MLMWH to catalyze or activate factor IIa (thrombin) inhibition by antithrombin) is the same as its anti-factor Xa activity (i.e., the ability to catalyze factor Xa inhibition by antithrombin). In contrast, LMWH has greater anti-factor Xa activity than anti-factor IIa activity because more than half of the chains of LMWH are too short to bridge antithrombin to thrombin. Although unfractionated heparin also has equivalent anti-factor Xa and anti-factor IIa activity, it differs from MLMWH in that it cannot catalyze thrombin inactivation in the presence of fibrin because the chains of unfractionated heparin are long enough to not only bridge antithrombin to thrombin, but also to bridge thrombin to fibrin.

In its typical configuration, the specific activity of MLMWH is similar to that of unfractionated heparin. Thus, its anti-factor Xa and anti-factor IIa activity ranges from 90 to 150 U/mg and 40 to 100 U/mg, respectively. In contrast, LMWH typically has a specific anti-factor Xa activity of 100 U/mg, whereas its anti-factor IIa activity ranges from 20 to 50 U/mg, depending on the molecular weight profile of the particular LMWH preparation.

C. Comparison of the Efficacy and Safety of the MLMWH Compounds of the Present Invention with Other Known Anticoagulants This example illustrates a study comparing the efficacy and safety of the MLMWH compounds of the present invention, which are denoted in the figures as V21, LMWH, heparin and hirudin in a the rabbit arterial thrombosis prevention model. The results are very promising since they indicate that the MLMWH compounds of the present invention are more effective than LMWH and heparin and safer than hirudin. The arterial thrombosis prevention model was modified so that both efficacy and safety could be assessed in the same animal. Efficacy was assessed by measuring flow over 90 minutes distal to a 95% stenosis in an injured rabbit aorta, and safety was assessed by measuring blood loss over 30 minutes using the rabbit ear model. The four compounds were compared at three dosage levels. Each compound was administered as a bolus and infusion for 90 minutes. The doses listed in the following figures represent the bolus and infusion/60 minutes, administered for 90 minutes. The doses for heparin are shown as units/Kg, for LMWH and V21 as mg/Kg and for hirudin as mg/Kg. V21 has similar anti-Xa activity to LMWH and about twice the anti-IIa activity of LMWH. Thus, the specific activity of LMWH is 100 anti-Xa/mg and 30 anti-IIa units/mg. The specific activity of V21 is 100 anti-Xa units/mg and 60 anti-IIa units/mg, whereas the specific activity of heparin is about 150 anti-Xa units and 150 anti-IIa units/mg. The anticoagulants were compared in the following dosages. Heparin 50 units/Kg and 75 unit/Kg; LMWH and V21 0.5, 1.0 and 1.5 mg/Kg; Hirudin 0.1/0.1, 0.1/0.2 and 0.1/0.3 mg/Kg.

For comparative purposes, 50 units of heparin is equivalent to 0.5 mg of LMWH or V21 in terms of anti-Xa activity, but has more than twice the anti-IIa activity of 0.5 mg of V21 and about 4 times the anti-IIa activity of LMWH. For equivalent anti-Xa activity, V21 has about twice the anti-IIa activity of LMWH.

Figure 11:
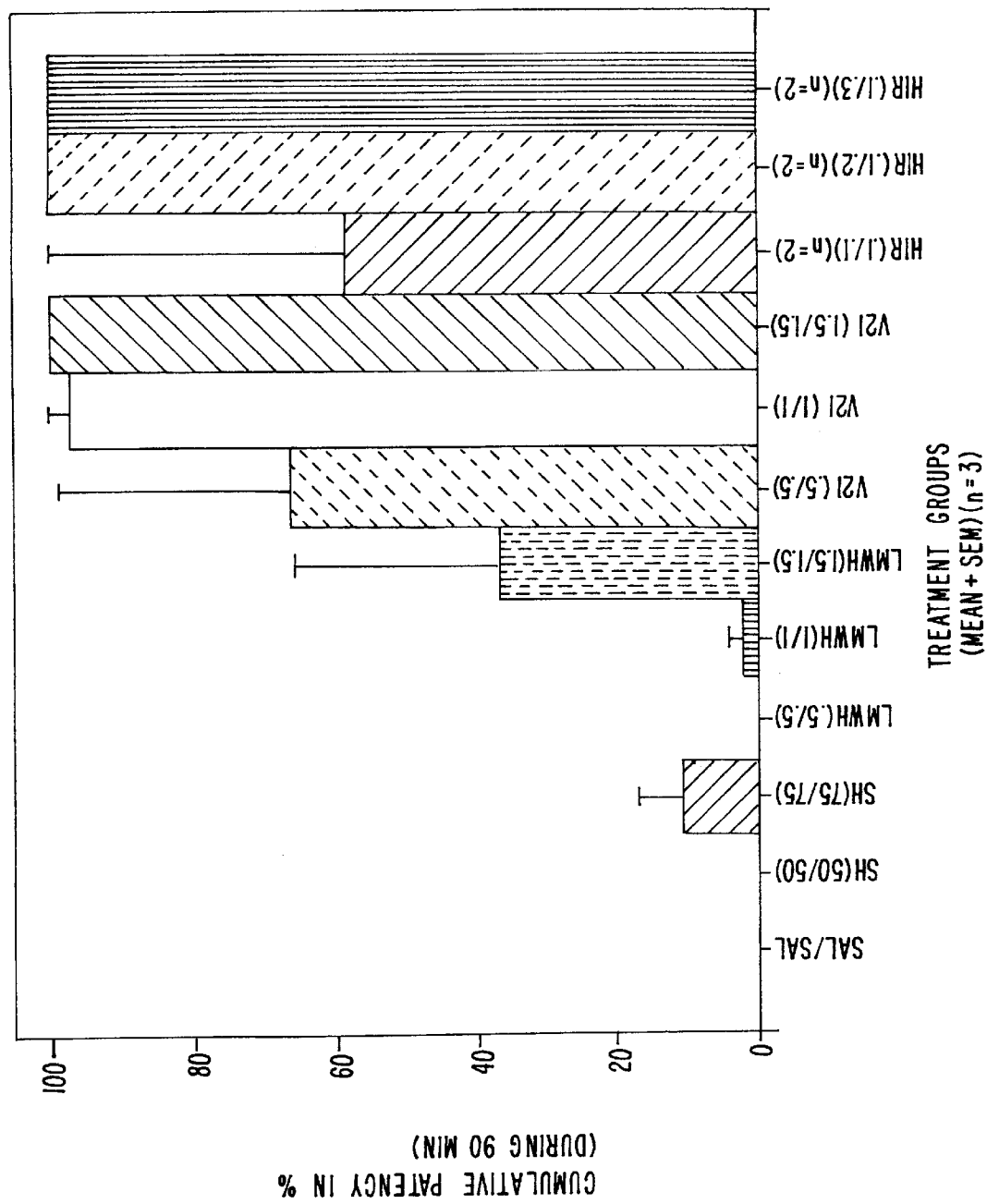
FIG. 11 illustrates the cumulative patency in % of standard heparin (SH), low molecular weight heparin (LMWH), MLMWH of the present invention (V21) and hirudin (HIR) in the prevention model study.
Figure 12:
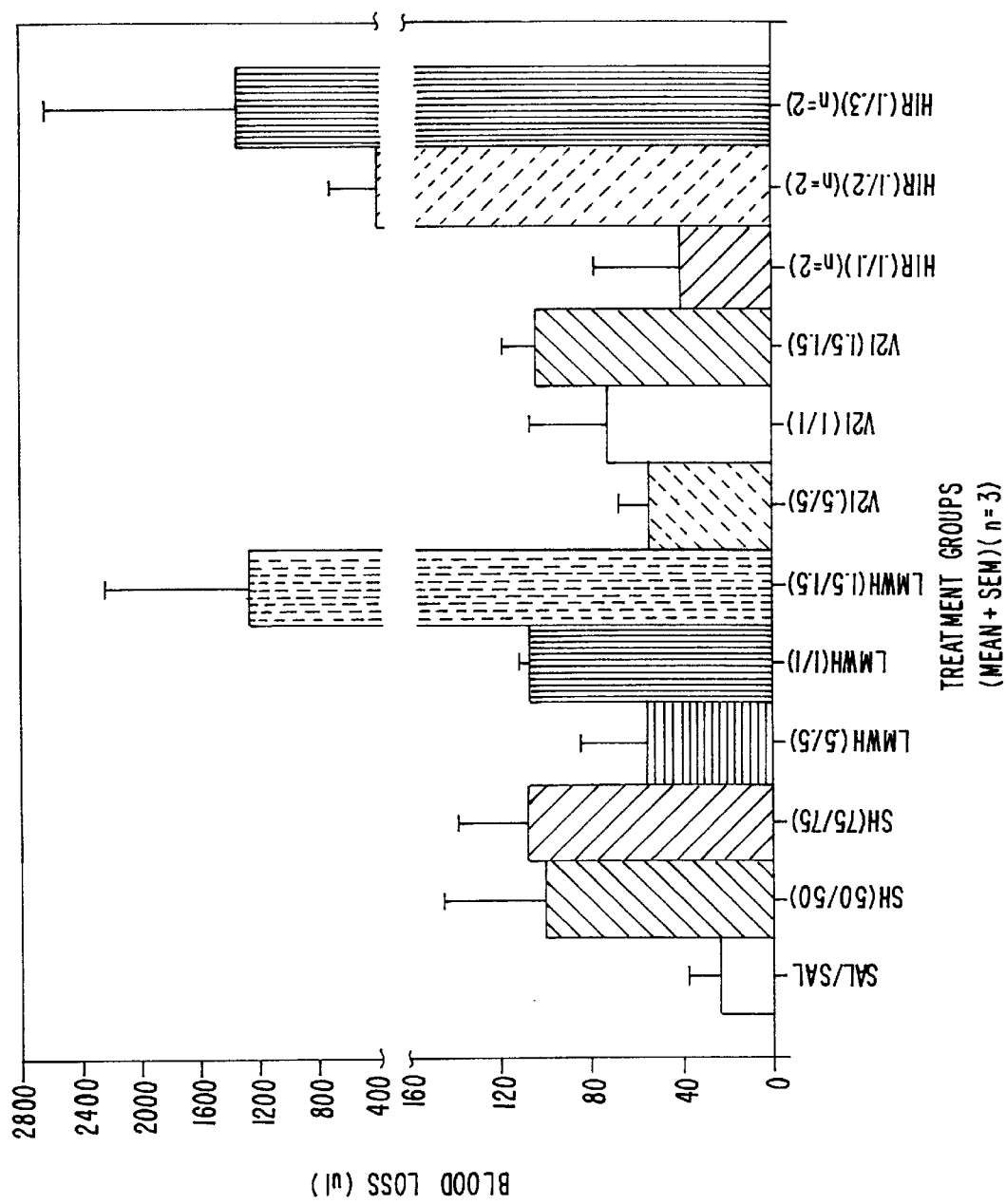
FIG. 12 illustrates the effect of standard heparin (SH), low molecular weight heparin (LMWH), the MLMWH compounds of the present invention (V21) and hirudin (HIR) on cumulative blood loss at 30 minutes.
Figure 13B:
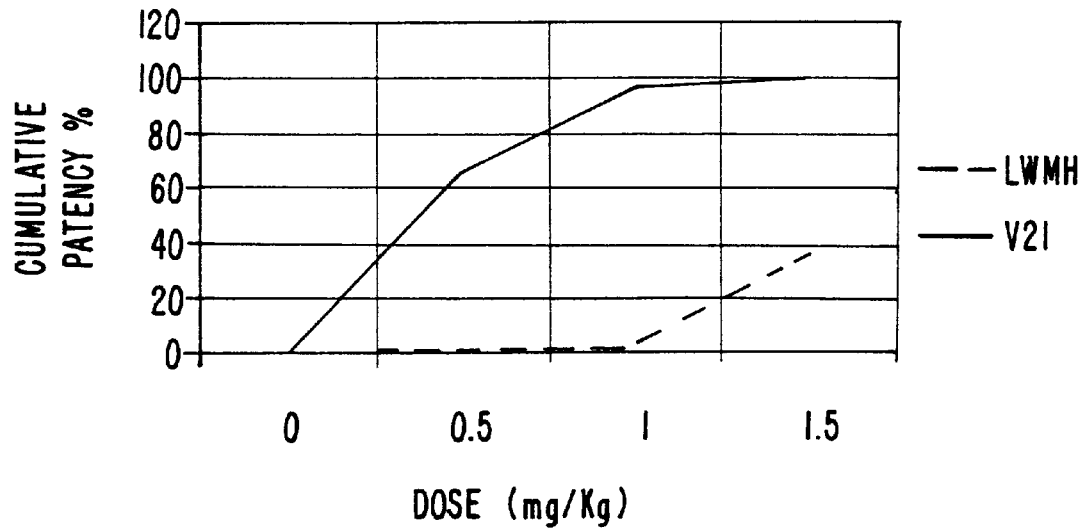
FIGS. 13A and 13B illustrate the efficacy of LMWH and the MLMWH compounds of the present invention (V21) in the arterial thrombosis model (A), and the effect of LMWH and the MLMWH compounds of the present invention (V21) on blood loss (B).
Figure 13A:
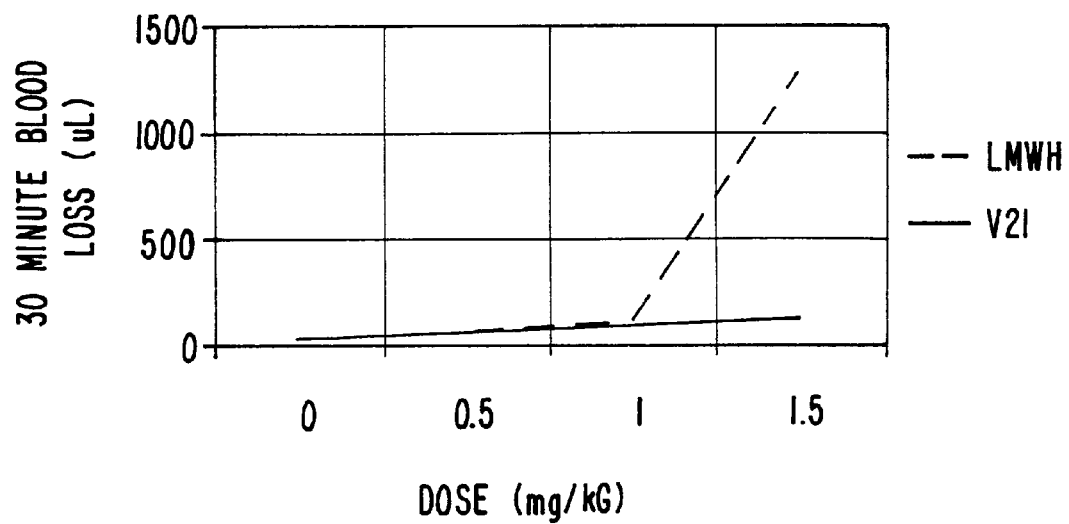

The results obtained during this study are set forth in FIGS. 11, 12 and 13. FIG. 11 compares the efficacy of the four anticoagulants using cumulative time that the aorta remained patent over the 90 minutes of observation as the outcome measure of efficacy. One hundred percent accumulated patency reflects complete patency and 0% cumulative patency reflects immediate and sustained thrombotic occlusion. The stenosed aorta clotted immediately and remained occluded for the full 90 minutes in the control animals, in the rabbits treated with low dose heparin (50/50 unit/Kg) and low dose LMWH (0.5/0.5 mg/Kg). There was a dose response with all four anticoagulants. However, the model was resistant to the antithrombotic effects of heparin and LMWH. Thus, both heparin in a dose of 75/75 units/Kg and LMWH in a dose of 1.0 mg/1.0 mg/Kg were ineffective (percent cumulative patency of 14% and 2% respectively), and LMWH 1.5/1.5 mg/Kg showed only limited effectiveness (38% cumulative patency). In contrast, the model was very responsive to the antithrombotic effects of V21 and hirudin. Thus, V21 at a dose of 0.5/0.5 mg/Kg was more effective than heparin at a dose of 75/75 units/Kg and more effective than LMWH in doses of 1.0/1.0 mg/Kg and 1.5/1.5 mg/Kg. Thus, V21 was at least three fold more potent than LMWH.

FIG. 12 illustrates the effects of the four anticoagulants on 30 minute blood loss. A dose response was observed with LMWH, V21 and hirudin. At doses that showed greater efficacy, V21 was much safer than LMWH, and at doses that showed equivalent efficacy, V21 was safer than hirudin. V21 was also much more effective than heparin at doses that produced a similar degree of blood loss.

The comparative safety and efficacy of V21 and LMWH is illustrated in FIG. 13. Based on the data (i.e., three animals in each group), V21 appears to about 4 times more potent than LMWH on a weight basis. Therefore, for equivalent anti-Xa activity, V21 is 4 time more potent than LMWH, and for equivalent anti-IIa activity, V21 is about twice as potent. Such data support the importance of fibrin-bound thrombin in promoting thrombogenesis, since V21 is more effective against fibrin-bound thrombin than LMWH or heparin. At doses of 0.5 mg/Kg and 1.0 mg/Kg, V21 appears to be as safe as LMWH (although it is much more effective), but at a dose of 1.5 mg/Kg, LMWH produced much more bleeding than V21. Thus, V21 appears to have a more favorable efficacy to safety profile than LMWH.

D. Preparation of the MLMWH Compounds of the Present Invention by a Limited Periodate Oxidation/Hydrolysis of Heparin 1.1 Study of Limited Periodate Oxidation/Hydrolysis of Heparin Heparin was dissolved in deuterated water to make 10% of stock solution. Sodium periodate was dissolved in deuterated water to make 100 mM stock solution and kept at 4° C. The periodate oxidation reaction was carried out at 2.5% of heparin concentration with increasing sodium periodate concentration, 1 mM, 2.5 mM, 5 mM, 8 mM, 10 mM, and 20 mM, at room temperature for about 18 hours. The reaction was stopped by adding 50 mM of ethylene glycol and incubation for 30 minutes. Then, the reaction mixture was brought to 0.25 N NaOH and incubated at room temperate for 3 hours. After the reaction, the pH was adjusted to pH 7 by 6 N HCl. An aliquot of each reaction mixtures was an HPLC-GPC (G2000 column, 0.5 ml/min, injection volume 20 μl) for molecular weight analysis. The molecular weight profiles of the reaction at sodium periodate concentration of 5 mM, 8 mM, 10 mM, and 20 mM decrease in comparison to heparin with increasing sodium periodate concentration. The result indicated that the desired cleavage can be achieved using sodium periodate concentrations of between about 5 mM and about 20 mM, and at room temperature for about 18 hours. The study (not shown) indicated that the best alkaline hydrolysis can be achieved using 0.25 N NaOH, at room temperature for 3 hours. Thus, the reaction condition used in this experiment are called "limited periodate/hydrolysis" conditions.

1.2 Preparation of MLMWH Compounds of the Present Invention by Limited Periodate Oxidation/Hydrolysis 100 mg of heparin was treated using the limited periodate/hydrolysis conditions, 7 mM sodium periodate, and purified by P30 gel-filtration chromatography. 30 mg of final product, i.e., V21-B5, was obtained having a molecular weight ranging from about 5000 Daltons to about 8400 Daltons, and having a peak molecular weight of about 7000 Daltons. 500 mg of heparin was treated using the limited periodate/hydrolysis conditions, 8 mM sodium periodate, and purified by P30 gel-filtration chromatography. 140 mg of final product, i.e., V21-B6, was obtained having a molecular weight ranging from about 5000 Daltons to about 8500 Daltons, and having a peak molecular weight of about 6500 Da.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A modified low molecular weight heparin (MLMWH) compound having a molecular weight of about 5,000 Daltons to about 9,000 Daltons, wherein said MLMWH compound has an anti-factor IIa activity of about 40 U/mg to about 100 U/mg, and an anti-factor Xa activity of about 90 U/mg to about 150 U/mg.

2. The MLMWH compound in accordance with claim 1, wherein said MLMWH compound (1) inhibits fibrin-bound thrombin and fluid-phase thrombin by catalyzing antithrombin, and (2) inhibits thrombin generation by catalyzing factor Xa inactivation by antithrombin.

3. The MLMWH compound in accordance with claim 1, wherein said MLMWH compound has an anti-factor IIa activity of about 60 U/mg to about 75 U/mg, and an anti-factor Xa activity of about 100 U/mg to about 125 U/mg.

4. The MLMWH compound in accordance with claim 3, wherein said MLMWH compound has an anti-factor IIa activity of about 65 U/mg, and an anti-factor Xa activity of about 115 U/mg.

5. The MLMWH compound in accordance with claim 1, wherein said MLMWH compound has a molecular weight of about 5,400 Daltons to about 8,000 Daltons.

6. The MLMWH compound in accordance with claim 1, wherein said MLMWH compound has a molecular weight of about 5,800 Daltons to about 7,000 Daltons.

7. The MLMWH compound in accordance with claim 1, wherein said MLMWH compound has a molecular weight of about 6,000 Daltons.

8. A method for treating a thrombotic condition in a mammal, said method comprising administering to said mammal a pharmacologically acceptable dose of a modified low molecular weight heparin (MLMWH) compound having a molecular weight of about 5,000 Daltons to about 9,000 Daltons, wherein said MLMWH compound has an anti-factor IIa activity of about 40 U/mg to about 100 U/mg, and an anti-factor Xa activity of about 90 U/mg to about 150 U/mg.

9. The method in accordance with claim 8, wherein said MLMWH compound (1) inhibits fibrin-bound thrombin and fluid-phase thrombin by catalyzing antithrombin, and (2) thrombin generation by catalyzing factor Xa inactivation by antithrombin.

10. The method in accordance with claim 8, wherein said MLMWH compound has an anti-factor IIa activity of about 60 U/mg to about 75 U/mg, and an anti-factor Xa activity of about 100 U/mg to about 125 U/mg.

11. The method in accordance with claim 10, wherein said MLMWH compound has an anti-factor IIa activity of about 65 U/mg, and an anti-factor Xa activity of about 115 U/mg.

12. The method in accordance with claim 8, wherein said MLMWH compound has a molecular weight of about 5,400 Daltons to about 8,000 Daltons.

13. The method in accordance with claim 8, wherein said MLMWH, wherein said MLMWH compound has a molecular weight of about 5,800 Daltons to about 7,000 Daltons.

14. The method in accordance with claim 8, wherein said MLMWH compound has a molecular weight of about 6,000 Daltons.

15. The method in accordance with claim 8, wherein said thrombotic condition is arterial thrombosis.

16. The method in accordance with claim 8, wherein said thrombotic condition is coronary artery thrombosis.

17. The method in accordance with claim 8, wherein said thrombotic condition is venous thrombosis.

18. The method in accordance with claim 8, wherein said thrombotic condition is pulmonary embolism.

19. The method in accordance with claim 8, wherein said MLMWH compound is administered by injection.

20. A method for preventing the formation of a thrombus in a mammal, said method comprising administering to said mammal a pharmacologically acceptable dose of a modified low molecular weight heparin (MLMWH) compound having a molecular weight of about 5,000 Daltons to about 9,000 Daltons, wherein said MLMWH compound has an anti-factor IIa activity of about 40 U/mg to about 100 U/mg, and an anti-factor Xa activity of about 90 U/mg to about 150 U/mg.

21. The method in accordance with claim 20, wherein said MLMWH compound (1) inhibits fibrin-bound thrombin and fluid-phase thrombin by catalyzing antithrombin, and (2) thrombin generation by catalyzing factor Xa inactivation by antithrombin.

22. The method in accordance with claim 20, wherein said MLMWH compound has an anti-factor IIa activity of about 60 U/mg to about 75 U/mg, and an anti-factor Xa activity of about 100 U/mg to about 125 U/mg.

23. The method in accordance with claim 22, wherein said MLMWH compound has an anti-factor IIa activity of about 65 U/mg, and an anti-factor Xa activity of about 115 U/mg.

24. The method in accordance with claim 20, wherein said MLMWH compound has a molecular weight of about 5,400 Daltons to about 8,000 Daltons.

25. The method in accordance with claim 20, wherein said MLMWH, wherein said MLMWH compound has a molecular weight of about 5,800 Daltons to about 7,000 Daltons.

26. The method in accordance with claim 20, wherein said MLMWH compound has a molecular weight of about 6,000 Daltons.

27. The method in accordance with claim 20, wherein said mammal is at increased risk of developing a thrombus due to a medical condition which disrupts hemostasis.

28. The method in accordance with claim 27, wherein said medical condition is coronary artery disease.

29. The method in accordance with claim 27, wherein said medical condition is atherosclerosis.

30. The method in accordance with claim 20, wherein said mammal is at increased risk of developing a thrombus due to a medical procedure.

31. The method in accordance with claim 30, wherein said medical procedure is cardiac surgery.

32. The method in accordance with claim 31, wherein said medical procedure is cardiopulmonary bypass.

33. The method in accordance with claim 30, wherein said medical procedure is catheterization.

34. The method in accordance with claim 33, wherein said catheterization is cardiac catheterization.

35. The method in accordance with claim 30, wherein said medical procedure is atherectomy.

36. A method for inhibiting thrombus formation in a mammal, said method comprising administering to said patient a pharmacologically acceptable dose of a modified low molecular weight heparin (MLMWH) compound having a molecular weight of about 5,000 Daltons to about 9,000 Daltons, wherein said MLMWH compound has an anti-factor IIa activity of about 40 U/mg to about 100 U/mg, and an anti-factor Xa activity of about 90 U/mg to about 150 U/mg.

37. The method in accordance with claim 36, wherein said MLMWH compound (1) inhibits fibrin-bound thrombin and fluid-phase thrombin by catalyzing antithrombin, and (2) thrombin generation by catalyzing factor Xa inactivation by antithrombin.

38. A method for inhibiting fibrin-bound thrombin and thrombin generation in a mammal, said method comprising administering to said mammal a pharmacologically acceptable dose of a modified low molecular weight heparin (MLMWH) compound having a molecular weight of about 5,000 Daltons to about 9,000 Daltons, wherein said MLMWH compound has an anti-factor IIa activity of about 40 U/mg to about 100 U/mg, and an anti-factor Xa activity of about 90 U/mg to about 150 U/mg.

39. A pharmaceutical composition comprising the MLMWH compound of claim 1 and a pharmaceutically acceptable carrier.

* * * * *

UNITED STATES PATENT AND TRADEMARK OFFICE
CERTIFICATE OF CORRECTION

PATENT NO. : 6,075,013
DATED : June 13, 2000
INVENTOR(S) : Jeffrey I. Weitz and Jack Hirsh It is certified that error appears in the above-identified patent and that said Letters Patent is hereby corrected as shown below:

Line 60,. Under Related U.S. Application Data, should read as follows: Provisional application No. 60/072,098, Jun 6, 1997, abandoned.

Signed and Sealed this

Fourth Day of December, 2001

*Attest:*

NICHOLAS P. GODICI
*Attesting Officer*    *Acting Director of the United States Patent and Trademark Office*